(12) United States Patent
Lautt

(10) Patent No.: US 8,017,575 B2
(45) Date of Patent: Sep. 13, 2011

(54) TREATMENT OF INSULIN RESISTANCE BY MODULATING SOMATOSTATIN USING SOMATOSTATIN RECEPTOR ANTAGONISTS

(76) Inventor: Wilfred Wayne Lautt, Winnipeg (CA)

( * ) Notice: Subject to any disclaimer, the term of this patent is extended or adjusted under 35 U.S.C. 154(b) by 784 days.

(21) Appl. No.: 11/721,908

(22) PCT Filed: Dec. 15, 2005

(86) PCT No.: PCT/CA2005/001920
§ 371 (c)(1),
(2), (4) Date: May 21, 2008

(87) PCT Pub. No.: WO2006/063465
PCT Pub. Date: Jun. 22, 2006

(65) Prior Publication Data
US 2009/0270311 A1    Oct. 29, 2009

Related U.S. Application Data

(60) Provisional application No. 60/636,034, filed on Dec. 15, 2004.

(51) Int. Cl.
*A61K 38/31* (2006.01)

(52) U.S. Cl. ........................................ 514/7.1

(58) Field of Classification Search .................. None
See application file for complete search history.

(56) References Cited

U.S. PATENT DOCUMENTS

| | | | |
|---|---|---|---|
| 4,505,897 A | 3/1985 | Coy et al. |
| 4,508,711 A | 4/1985 | Coy et al. |
| 5,846,934 A | 12/1998 | Bass et al. |
| 5,925,618 A | 7/1999 | Baumbach et al. |
| 6,602,849 B1 | 8/2003 | Gordon |
| 7,238,695 B2 | 7/2007 | Thurieau et al. |
| 2004/0181032 A1 | 9/2004 | Coy et al. |

FOREIGN PATENT DOCUMENTS

| | | |
|---|---|---|
| WO | WO 99/52875 | 10/1999 |
| WO | WO 99/65942 | 12/1999 |

OTHER PUBLICATIONS

Branch et al., 1973, "The reduction of lidocain clearance by *dl*-propranolol: An example of hemodynamic drug interaction." *J Pharmacol Exp Ther* 184(2) 515-519.
Hiebert et al., 1972, "Direct Measurement of Insulin Secretory Rate: Studies in Shocked Primates and Posoperative Patients." *Ann Surg* 176: 296-304.
Hiebert et al., 1976, "Species differences in insulin secretory responses during hemorrhagic shock." *Surgery* 79(4):431-455.
Kobayashi et al.(1991), "Some metaqbolic actions of imidazoline sympathomimetics: Hyperglycemia and lipid mobilization." *J. Pharmacol* 22, 66.
Latour et al., 2002, "The hepatic vagus nerve in the control of insulin sensitivity in the rat." *Autonomic Neurosci* 95: 125-130.
Latour et al., 2002, "Insulin sensitivity regulared by feeding in the conscious untrained rat." *Can J Physiol Pharmacol* 80:8-12.
Lautt, 1999, "The HISS story overview: a novel hepatic neurhumoral regulation of peripheral insulin sensitivity in health and diabetes." *Can J Physiol Pharmacol* 77:553-562.
Lautt, 2004, "A new paradigm for diabetes and obesity: the hepatic insulin sensitizing substance (HISS) hypothesis." *J. Pharmacol Sci* 95: 9-17.
Lautt et al., 1976, "The effect of SKF-525A and of altered hepatic blood flow in lidocain clearance in the cat." *Can J Physiol Pharmacol* 55:7-12.
Lautt et al., 1982, "Control of the hyperglycemic response to hemorrhage to cats." *Can J Physiol* 60: 1618-1623.
Lautt et al., 1998, "Rapid insulin sensitivity test (RIST)." *Can J Physiol Pharmacol* 76: 1080-1086.
Lautt et al., 2001, "Hepatic parasympathetic nerve-dependent control of peripheral insulin sensitivity." *Am J Physiol Gastrointest Liver Physiol* 281: 29-36.
Lautt et al., 2004, "Pharmaceutical reversal of insulin resistance." *Proc West Pharmacol Soc* 47: 30-32.
Lautt, 2005, "Insulin sensitivity in skeletal muscle regulated by a hepatic hormone, HISS." *Can App Physiol* 30: 3: 304-312.
Ma et al., 2003, "Hemorrhage induces the rapid development of hepatic insulin resistance ." *Am J. Physiol Gastrointest Liver Physiol* 284:107-115.
Mason et al., 1975, "A historical view of the stress field." *J. Human Stress* 1:1: 6-12.
Messerli et al., 1977, "Effects of angiotensin II on steroid metabolism and hepatic blood flow in man." *Circulation Research* 40: 204-207.
Nettelbladt et al., 1996, "Pre-stress carbohydrate solution prevents fatal outcome after hemmorhage in 24-hour food-deprived rats." *Nutrition* 12 (10): 696-699.
Robertson et al., 1973, "Adrenergic modulation of basal insulin secretion in man." *Diabetes* 22: 1-8.
Sadri et al., 1998, "Blockade of nitric oxide production in the liver causes insulin resistance." *Proc West Pharmacol Soc* 41:37-38.
Sadri et al., 1999, "Blockade of hepatic nitric oxide synthase causes insulin resistance." *Am J Physiol* 277:101-108.
Sadri et al., 2000, "Insulin Resistance Cause by Hepatic COX Inhibition." *Diabetes* 49:A245.
Seredycz et al., 2006, "Acute hemmorhage causes hepatic insulin sensitizing substance (HISS)-dependent insulin resistance." *Can J Physiol Pharmacol* 84: 1145-1151.
Shen et al., 1982, "Human somatostatin I: Sequence of the cDNA." *Proc Natl Acad Sci USA* 79: 4575-4579.

(Continued)

*Primary Examiner* — Christina Bradley
(74) *Attorney, Agent, or Firm* — Merchant & Gould P.C.; Brian R. Dorn

(57) ABSTRACT

The present invention provides the use of somatostatin antagonists for treating and preventing HISS-dependent insulin resistance and hemorrhage induced insulin resistance. The present further provides pharmaceutical compositions comprising a somatostatin antagonist and a pharmaceutically acceptable liver targeting compound.

11 Claims, 12 Drawing Sheets

OTHER PUBLICATIONS

Takayama et al., 2000, "Dose-related atropine-induced insulin resistance: comparing intraportal versus intravenous administration." *Proc West Pharmacol Soc* 43: 33-34.

Thorell et al., 1999, "Insulin resistance: a marker of surgical stress." *Curr Opin Clin Nutr Metab Care* 2:69-78.

Xie et al., 1994, "Insulin resistance produced by hepatic denervation or muscarinic cholinergic blockade." *Proc West Pharmacol Soc* 37: 39-40.

Xie et al., 1995, "Induction of insulin resistance by cholinergic blockade with atropine in the cat." *J Anton Pharmacol* 15: 361-369.

Yamaguchi et al., 1992, "Sympathoadrenal system in neuroendocrine control of glucose: mechanisms involved in the liver, pancreas, and adrenal gland under hemorrhagic and hypoglycemic stress." *Can J Physiol Pharmacol* 70(2): 167-206.

Yates et al. (1965), "Contributions of the liver to steady-state performance and transient responses of the adrenal cortical system." *Fed Proc* 24: 723-730.

TREATMENT OF INSULIN RESISTANCE BY MODULATING SOMATOSTATIN USING SOMATOSTATIN RECEPTOR ANTAGONISTS

This application is a national stage entry under 35 U.S.C. §3.71 of PCT/CA2005/001920, filed Dec. 15, 2005, which claims the benefit under 35 U.S.C. §119(e) of U.S. Provisional Application No. 60/636,034, filed Dec. 15, 2004, the entire disclosures of which are hereby incorporated by reference.

FIELD OF INVENTION

The present invention relates to methods and compounds useful for the treatment of insulin resistance, and in particular hemorrhage induced insulin resistance and HISS-dependent insulin resistance.

BACKGROUND

Elective surgery and resulting blood loss are often associated with increases in insulin resistance of magnitudes of 50% or greater following uncomplicated surgical operations (Thorell, Anders, Nygren, Jonas; Ljungqvist, Olle. Insulin resistance: a marker of surgical stress. Curr Opin Clin Nutr Metab Care 2:69-78, 1999). It is not clear which mediators are most crucial for the development of insulin resistance following surgery and hemorrhage. Hemorrhage is a useful model of acute stress because it can be quantified in anaesthetized animals and results in a wide range of metabolic consequences including hyperglycemia and insulin resistance (Ma, Y., Want, P., Kuebler, J. F., Chaudry, I. H., Messina, J. L. Hemorrhage induced the rapid development of hepatic insulin resistance. *Am J Physiol Gastrointest Liver Physiol.*: 284: G107-G115, 2002).

Elevations in plasma glucose levels following rapid blood loss are mediated primarily through the hepatic sympathetic nerves and the adrenals (Lautt, W. W., Dwan, P. D., Singh, R. R. Control of the hyperglycemic response to hemorrhage to cats. *Can J Physiol Pharmacol.* 60:1618-1623, 1982). The activation of this redundant control system in response to hemorrhage initiates several compensatory responses, with the most crucial being glycogenolysis and insulin level reduction (Hiebert, J. M., J. M. McCormick, R. H. Egdahl. Direct measurement of insulin secretory rate: studies in shocked primates and postoperative patients. *Ann. Surg:* 176:296-304, 1972. Hiebert, J. M., C. Kieler, J. S S S. Soldner, R. H Egdahl. Species differences in insulin secretory response during hemorrhagic shock. *Surgery:* 79:451-455, 1976). The attenuation in insulin levels following hemorrhage are physiologically advantageous, as glucose can be utilized for life-sustaining systems and osmotic mobilization of extravascular fluid into the circulation (Yamaguchi, N. Sympathoadrenal system in neuroendocrine control of glucose: mechanisms involved in the liver, pancreas, and adrenal gland under hemorrhagic and hypoglycemic stress. *Can J Physiol Pharmacol.* 70(2):167-206, 1992). Thus, survival following a severe hemorrhage is closely related to the capacity of the animal to develop hyperglycemia (Nettelbladt, C. G., Aligobevic, A., Ljungqvist, O., Pre-stress carbohydrate solution prevents fatal outcome after hemorrhage in 24 hour food deprived rats. *Nutrition* 12:10: 696-699, 1996).

The present inventors have recently described a novel mechanism of insulin resistance. Postprandial insulin causes the release of a Hepatic Insulin Sensitizing Substance (HISS), which acts selectively on skeletal muscle to stimulate glucose uptake. HISS-dependent insulin action accounts for approximately 55% of total insulin action in the fed state (Lautt W. W., Macedo M P, Sadri, P., Takayama, S., Ramos, F. D., Legare, D. J. Hepatic parasympathetic nerve-dependent control of peripheral insulin sensitivity is determined by feeding and fasting: dynamic control of HISS-dependent insulin action. *Am J Physiol. Gastrointest. Liver Physiol.* 281:G29-G36, 2001). The blockade of HISS release or action leads to a state of insulin resistance known as HISS-dependent insulin resistance (HDIR). HDIR is seen in a wide variety of pathological models including; fasting (Lautt et al., 2001), hepatic muscarinic cholinergic blockade with atropine (Xie, H. and Lautt, W. W. Induction of insulin resistance by cholinergic blockade with atropine in the cat. *J. Auton. Pharmacol.* 15:361-369, 1995. Xie, H. and Lautt, W. W. Insulin resistance produced by hepatic denervation or muscarinic cholinergic blockade. *Proc. West. Pharmacol. Soc.* 37:39-40, 1994), hepatic nitric oxide synthase blockade with L-NMMA or L-NAME (Sadri, P. and Lautt, W. W. Blockade of hepatic nitric oxide synthase causes insulin resistance. *Am. J. Physiol.* 277:G101-G108, 1999. Sadri, P. and Lautt, W. W. Blockade of nitric oxide production in the liver causes insulin resistance. Proc. West. Pharmacol. Soc. 41:37-38, 1998), hepatic cyclooxygenase inhibition (Sadri, P. and Lautt W. W. Insulin resistance caused by hepatic COX inhibition. *Diabetes:* 49(Suppl 1):A245, 2000), or surgical denervation of the liver (Xie, H. and Lautt, W. W. Insulin resistance produced by hepatic denervation or muscarinic cholinergic blockade. *Proc. West. Pharmacol. Soc.* 37:39-40, 1994. Latour, M. G. and Lautt, W. W. The hepatic vagus nerve in the control of insulin sensitivity in the rat. *Autonomic Neurosci.* 80:8-12, 2002). HDIR has been suggested to account for postprandial hyperglycemia, hyperinsulinemia, and hyperlipidemia (Lautt, W. W., A new paradigm for diabetes and obesity: The hepatic insulin sensitizing substance (HISS) hypothesis. *J. Pharmacol. Sci.* 95:9-17, 2004). Most recently, the present inventors have shown that hemorrhage demonstrates insulin resistance that is totally accountable for by HDIR. (Seredycz, L., Ming, X., Lautt, W. W. Acute hemorrhage causes HISS-dependent insulin resistance. Submitted to the American Journal of Physiology in 2004).

The response to stress and surgical trauma has been described as a multi-hormonal reaction that is designed to act in a selective manner specific to the stimulus imposed upon it (Mason, J. W., Wherry, F. E., Pennington, L. L., Spector, N. H. A historical view of the stress field. J. Human Stress. March; 1(1):6-12, 1975). Regulators of the hemorrhagic response that induce HDIR may include the hepatic sympathetic nerves and the endocrine system. The blockade of alpha and beta hepatic receptors may assist in the prevention of HDIR following hemorrhage as adrenergic stimulation is partially responsible for the regulation of insulin and glucagon release in response to stress, and may regulate the basal secretion of insulin (Robertson, R. P., Porte, D. Adrenergic modulation of basal insulin secretion in man. Diabetes 1973; 22:1-8). Somatostatin, a poorly understood hormone, is a potent inhibitor of insulin and glucagon and may also play a key role in initiating HDIR, as levels in cats are shown to increase dramatically following hemorrhage (Lautt, W. W., Dwan, P. D., Singh, R. R. Control of the hyperglycemic response to hemorrhage to cats. *Can J Physiol Pharmacol.* 60:1618-1623, 1982).

SUMMARY OF INVENTION

In an attempt to elucidate how hemorrhage induces HDIR, the inventors hypothesized that antagonism of one of the above neuroendocrine responses could prevent HDIR subsequent to hemorrhage. The present inventors have now determined that the state of HDIR following hemorrhage is not formulated by alpha or beta adrenergic responses, but caused by somatostatin, and can be prevented via a somatostatin receptor antagonist. Furthermore, the inventors have now determined that the activation of the sympathetic nerves can initiate the concomitant release of somatostatin subsequent to hemorrhage.

The present invention teaches a method of treating HISS-dependent insulin resistance comprising administering a therapeutically effective amount of a somatostatin antagonist to a patient in need thereof.

The present invention teaches a method of treating hemorrhage induced insulin resistance comprising administering a therapeutically effective amount of a somatostatin antagonist to a patient in need thereof. The hemorrhage may be the result of a surgical intervention or an injury. The hemorrhage induced insulin resistance may be HISS-dependent insulin resistance In an embodiment the somatostatin antagonist is cyclosomatostatin.

In a further embodiment of the invention, therapeutically effective amount of cyclosomatostatin is between 1 and 1000 µg/kg patient weight, 1 and 100 µg/kg patient weight, or 10 and 50 µg/kg patient weight.

In a still further embodiment of the invention, the therapeutically effective amount of cyclosomatostatin is about 20 µg/kg patient weight.

In yet another embodiment of the invention, the somatostatin antagonist is selected from a group consisting of DC-41-33, BIM-23454, SB-710411, cyclo (7-aminoheptanoyl-Phe-D-Trp-Lys-O-benzyl-Thr) and AC-178,335 and a combination thereof.

The present invention teaches use of a somatostatin receptor antagonist and a pharmaceutically acceptable liver targeting substance for the preparation of a medicament.

The present invention teaches a pharmaceutical composition comprising a somatostatin receptor antagonist and a pharmaceutically acceptable liver targeting substance.

In an embodiment of the invention, the pharmaceutical composition comprises cyclosomatostatin as the somatostatin receptor antagonist.

In another embodiment of the invention, the pharmaceutical composition comprises DC-41-33, BIM-23454, SB-710411, cyclo (7-aminoheptanoyl-Phe-D-Trp-Lys-O-benzyl-Thr) and AC-178,335 or a combination thereof as the somatostatin receptor antagonist.

In a further embodiment of the invention, the liver targeting substance is selected from a group consisting of: albumin, a liposome, and a bile salt.

DETAILED DESCRIPTION

Figure 1:
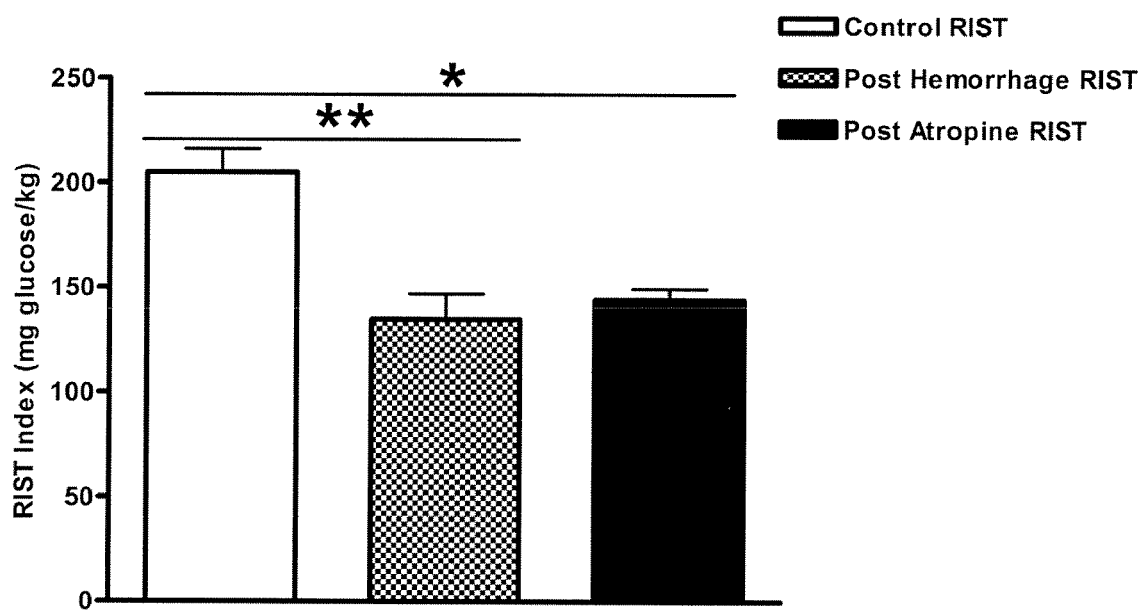
FIG. 1 is a bar graph comparing the effect of hemorrhage and hemorrhage followed by atropine administration on the RIST index.

Hemorrhage is known to induce insulin resistance. The present inventors have now characterized hemorrhage induced insulin resistance as being HISS-dependent insulin resistance (HDIR) which results from the blockade of HISS release or HISS action. The present inventors have determined that hemorrhage induced HDIR is caused by somatostatin inhibiting the release of HISS in the liver. The present inventors have further determined that somatostatin receptor antagonists are useful for treating hemorrhage induced HDIR.

Somatostatin is known to block insulin action by inhibiting the release of insulin. The use of somatostatin antagonists for increasing the release or production of insulin has previously been suggested. For example, U.S. Pat. Nos. 4,505,897 and 4,508,711 teach the use of cyclic pentapeptides for increasing the release of insulin. U.S. Pat. Nos. 5,846,934 and 5,925,618 discloses novel peptide somatostatin receptor antagonist and uses thereof for increasing insulin release or production. U.S. Patent Application 20040181032 also disclose novel peptide somatostatin receptor antagonists. U.S. Patent Application 20040176379 discloses imidazolyl derivatives having somatostatin receptor antagonism properties and use of the derivatives for treating diabetes and insulin insensitivity. U.S. Pat. No. 6,602,849 discloses cyclic somatostatin analogs having somatostatin receptor antagonism properties and use of the derivatives for treating diabetes and insulin insensitivity.

The present inventors have now discovered a new and novel use for somatostatin antagonist receptors. The present inventors are the first to disclose the use of somatostatin receptor antagonists for treating hemorrhage induced insulin resistance, and more particularly, HDIR. The present inventors are the first to report the usefulness of somatostatin receptor antagonist for treating HDIR which is not relieved by increased insulin production or release.

Pharmaceutical Compositions

In view of the inventor's discoveries, the invention provides pharmaceutical compositions useful for treating hemorrhage induced insulin resistance and in particular, HISS-dependent insulin resistance. The pharmaceutical compositions according to the invention comprise a somatostatin receptor antagonist and a pharmaceutically acceptable liver targeting compound.

As used herein, the term "somatostatin receptor antagonist" includes any compound capable of partially or completely inhibiting the effects of somatostatin, including in particular type 2 receptor antagonists.

In an embodiment of the invention, the somatostatin receptor antagonist is cyclosomatostatin. Other somatostatin receptor antagonists which may be used to prepare the pharmaceutical composition according to the invention include, but are not limited to: cyclo (7-aminoheptanoyl-Phe-D-Trp-Lys-O-benzyl-Thr) and derivatives thereof disclosed in U.S. Pat. No. 4,505,897, the cyclic pentapeptide antagonists disclosed in U.S. Pat. Nos. 4,508,711 and 4,505,897, the peptide antagonists disclosed in U.S. Pat. Nos. 5,846,934 and 5,925,618 and U.S. Patent Application 20040181032, and the imadazoly derivatives disclosed in U.S. Patent Application 20040176379. Further somatostatin receptor antagonists which may be used to prepare the pharmaceutical composition according to the invention include: DC-41-33, BIM-23454, SB-710411, and AC 178,335

The pharmaceutical compositions of the present invention also comprise pharmaceutically acceptably liver-targeting compounds. The inclusion of a liver-targeting compound allows the pharmaceutical compositions to be targeted to the liver of the patient thereby eliminating deleterious systemic effects. The somatostatin receptor antagonist can be conjugated to bile salts or albumin for preferential delivery to the liver. Alternatively, the somatostatin receptor antagonist can be encapsulated within liposomes which are preferentially targeted to the liver.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The pushfit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e. g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e. g., by bolus injection or continuous infusion. Formulations for injection may be presented in unit dosage form, e. g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e. g., sterile pyrogen-free water, before use.

The compounds may also be formulated in rectal compositions such as suppositories or retention enemas, e. g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied.

Alternatively, other delivery systems for hydrophobic pharmaceutical compounds may be employed.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients.

Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Methods of Treatment

The present invention provides a method of treating hemorrhage induced insulin resistance comprising the administration of a therapeutically effective amount of a somatostatin receptor antagonist to a patient in need thereof. In an embodiment of the invention, the hemorrhage induced insulin resistance is HISS-dependent insulin resistance. The hemorrhage may be the result of a surgical intervention or an injury. For example, the hemorrhage may be the result of a surgical intervention in highly vacularized tissue such as heart surgery, lung surgery, intestinal surgery, kidney surgery. The hemorrhage may also be the result of trauma from an accident, such as car accident, and may include internal bleeding or shock.

By an "effective amount" or a "therapeutically effective amount" of a pharmacologically active agent is meant a nontoxic but sufficient amount of the drug or agent to provide the desired effect. In a combination therapy of the present invention, an "effective amount" of one component of the combination is the amount of that compound that is effective to provide the desired effect when used in combination with the other components of the combination. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The therapeutic effective amount of any of the active agents encompassed by the invention will depend on number of factors which will be apparent to those skilled in the art and in light of the disclosure herein. In particular these factors include: the identity of the compounds to be administered, the formulation, the route of administration employed, the patient's gender, age, and weight, and the severity of the condition being treated and the presence of concurrent illness affecting the gastrointestinal tract, the hepatobillary system and the renal system. Methods for determining dosage and toxicity are well known in the art with studies generally beginning in animals and then in humans if no significant animal toxicity is observed. The appropriateness of the dosage can be assessed by monitoring insulin resistance using the RIST protocol as set out in Lautt et al, 1998. Where the dose provided does not cause insulin resistance to decline to normal or tolerable levels, following at least 24 hours of treatment, the dose can be increased. The patient should be monitored for signs of adverse drug reactions and toxicity, especially with regard to liver function.

Any of the somatostatin receptor antagonists described above can be used to treat hemorrhage induced insulin resistance and HISS-dependent insulin resistance. For administration to mammals, and particularly humans, it is expected that the daily dosage level of the somatostatin receptor antagonist will be from 0.001 mg/kg to 10 mg/kg, typically between 0.01 mg/kg and 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In a preferred embodiment of the invention, the somatostatin receptor antagonist employed is cyclosomatostatin. The therapeutically effective amount of the cyclosomatostatin will generally be between 1 and 1000 µg/kg patient weight. The amount of cyclosomatostatin may be between 1 and 100 µg/kg patient weight. The amount of cyclosomatostatin may be between 10 and 50 µg/kg patient weight. In a further embodiment, the therapeutically effective amount of cyclosomatostatin is about 20 µg/kg patient weight.

It may be desirable to target the somatostatin receptor antagonist to the liver. Preferential delivery of the somatostatin receptor antagonist can be achieved by conjugating the antagonist with albumin or a bile salt or by encapsulating the antagonist within a liposome. Where the somatostatin receptor antagonist is targeted to the liver, the dosage may be reduced.

Although the invention has been described with reference to illustrative embodiments, it is to be understood that the invention is not limited to these precise embodiments, and that various changes and modifications may be effected therein by one skilled in the art. All such changes and modifications are intended to be encompassed in the appended claims.

Experimental Materials and Methods

Surgical Procedures: Male Sprague Dawley rats (Charles River, St. Constant, Quebec, Canada) were housed in climate-controlled conditions for at least 6 days prior to surgical preparation. The animals were fasted for 8 hours, and then allowed ad lib access to standard rat chow for 2 hours prior to surgical preparation. This re-feeding protocol was used to ensure that all rats had recently eaten as HISS release occurs maximally in the early postprandial state and decreases progressively with fasting duration (Lautt W W, Macedo M P, Sadri P, Takayama S, Ramos F D, and Legare D J. Hepatic parasympathetic nerve-dependent control of peripheral insulin sensitivity is determined by feeding and fasting: dynamic control of HISS-dependent insulin action. *Am J Physiol Gastrointest Liver Physiol* 281: G29-G36, 2001). The animals were weighed and anesthetized by an intraperitoneal injection of pentobarbital sodium (65 mg/ml, Somnotol, Biomeda-MTC Animal Health Inc., Cambridge Canada). Temperature was monitored by a rectal thermometer and kept constant at 37.5±0.5° C. by a heated surgical table and an overhead lamp. The right femoral artery and vein were cannulated with catheters (polyethylene tubing PE60) that were connected with a silicon segment (Masterflex silicon tubing (Platinum) L/S 14), allowing blood to flow uninterrupted from the artery to the vein (Lautt W W, Wang X, Sadri P, Legare D J, and Macedo M P. Rapid insulin sensitivity test (RIST). *Can J Physiol Pharmacol* 76: 1080-1086, 1998). Animals were heparinized (100 IU/kg). Blood samples were taken by puncturing the arterial side of the arterial-venous shunt. The infusion of pharmacological agents was done by puncturing and inserting an infusion line into the silicon sleeve of the venous side of the shunt. Arterial pressure was measured by clamping the silicon sleeve on the venous side of the shunt, and measuring pressure from a side branch. A tracheotomy was performed (Micro-Renathane Tubing (095), Braintree Scientific Inc.) The left jugular vein was then cannulated with PE60 tubing in order to allow for continuous supplemental anesthetic (sodium pentobarbital, 2.16 mg/ml saline) infusion at a rate of 0.5 ml/hr/100 g of body weight. An infusion line was inserted into a silicon sleeve on the jugular supplement line for glucose administration and was controlled by a variable infusion pump (Genie, Kent Scientific Corporation, Litchfield, Mass.). The cannulation of the femoral artery and vein, the tracheotomy and the jugular vein cannulation is the standard surgical preparation. In scenarios where superior mesenteric artery occlusions were necessary, a laparotomy was performed.

RIST Methodology: The Rapid Insulin Sensitivity Test (RIST) was used to assess insulin sensitivity. After surgical completion, the animal was allowed to stabilize for 30 minutes, after which arterial blood samples (25 µl) were taken from the shunt and analyzed for blood glucose concentration using a glucose oxidase analyzer (Yellow Springs Instruments, Yellow Springs, Ohio). Samples were analyzed at five-minute intervals until 3 successive stable measurements were obtained. The mean of these 3 samples was used as the basal glucose level. After the basal glucose level was established, a bolus of insulin (50 mU/kg) was infused into the venous side of the shunt over 5 minutes at a rate of 0.1 ml/min. At 45 seconds, a glucose infusion was initiated and adjusted to maintain euglycemia as determined by the basal glucose level. An arterial sample was taken from the arterial-venous shunt every 2 minutes during the RIST, and the glucose infusion was increased or decreased accordingly. The RIST was complete when no further glucose was required, indicating the end of insulin and HISS action. The amount of glucose infused over the RIST (mg glucose/kg of body weight) is known as the RIST index. The RIST is capable of measuring both HISS-dependent and HISS-independent insulin action (Lautt W W, Wang X, Sadri P, Legare D J, and Macedo M P. Rapid insulin sensitivity test (RIST). *Can J Physiol Pharmacol* 76: 1080-1086, 1998).

Drugs: Human insulin (Humulin R) was purchased from Eli Lilly (Toronto, Canada). Atropine, D-glucose, phentolamine, isoproterenol, and cyclosomatostatin were purchased from Sigma Chemical Co. (St. Louis, Mo.). Propranolol hydrochloride USP was purchased from Sabex (QC, Canada). All drugs with the exception of cyclosomatostatin were dissolved in saline. Cyclosomatostatin was initially dissolved in twice-distilled water and then diluted in saline.

Data Analysis: Data were analyzed using repeated-measures and one-way ANOVA, followed by the Tukey-Kramer multiple comparison test in each group. The data were expressed as means±SE throughout. Differences were accepted as statistically significant at P<0.05. Animals were treated according to the guidelines of the Canadian Council on Animal Care, and the ethics committee on animal care at the University of Manitoba approved all protocols.

Example One

Hemorrhage Results in HISS-dependent Insulin Resistance (HDIR)

Following the standard surgical procedure described above, a control RIST was performed. The anesthetized animal was hemorrhaged to an arterial blood pressure of 50 mmHg and held at this pressure for a 10 minute interval, by withdrawing additional blood as needed. Blood was not returned. The animal was hemorrhaged from the arterial side of the shunt, using a 23-gauge needle attached to a syringe, at a rate of 0.5 ml/min. Arterial blood pressure was measured from the vascular shunt during brief occlusion of the venous side of the shunt. Following the hemorrhage, arterial blood glucose levels were measured until they became stable for at least 15 minutes and another RIST was performed. After stabilization following the RIST, atropine (1 mg/kg IV) was administered through the venous side of the shunt at a rate of 0.1 ml/min over 5 minutes. This dose of atropine results in a complete block of HISS release (Takayama S, Legare D J, and Lautt W W. Dose-related atropine-induced insulin resistance: comparing intraportal versus intravenous administration. *Proc West Pharmacol Soc* 43: 33-34, 2000). Following stabilization, a post atropine RIST was performed to quantify the RIST index during the complete absence of HISS action.

Result: Animals in this series (n=5; 247.6±6.7 grams) had an initial RIST index of 204.8±11.3 mg of glucose/kg, a post hemorrhage RIST index of 134.5±12.3 and a post atropine RIST index of 144.0±5.3 (FIG. 1). As shown in FIG. 1, the post hemorrhage RIST index decreased and was not decreased further by the administration of atropine thereby indicating that hemorrhage caused full HDIR (**P=0.001, *P=0.01). The decrease (34.3±4.8%) in insulin sensitivity between the control and the post hemorrhage RIST is significant (P=0.001). There was no statistical significance between the post hemorrhage and post atropine RIST. The amount of time taken to remove the volume of blood (3.3±0.7 ml) required to reduce mean arterial pressure to 50 mmHg was 4.1±0.9 minutes. Hyperglycemia was immediately present as basal glucose levels increased from a baseline of 109.5±5.0 to 127.3±6.3 mg/dl within 5 minutes of onset of hemorrhage. A partial restoration (50.0±0.0 to 63.1±3.8 mmHg) of mean arterial pressure was noted following hemorrhage prior to stabilization of arterial glucose levels and the post hemorrhage RIST. The suppression of HISS action after hemorrhage was complete, as shown by the inability of atropine to produce a further reduction. However, since full blockade of HISS action normally results in a decrease of approximately 55% of insulin action, and hemorrhage only resulted in a 34.3% reduction, other complicating factors were sought.

Discussion: Atropine administration (1 mg/kg-IV) results in the complete blockade of HISS and a 55% reduction in the RIST index (Xie H and Lautt W W. Induction of insulin resistance by cholinergic blockade with atropine in the cat. *J Auton Pharmacol* 15: 361-369, 1995. Xie H and Lautt W W. Insulin resistance produced by hepatic denervation or muscarinic cholinergic blockade. *Proc West Pharmacol Soc* 37: 39-40, 1994). Given that the post hemorrhage RIST caused a decrease in insulin sensitivity that was not decreased further by the administration of atropine, it was concluded that hemorrhage caused the complete suppression of HISS action and led to HDIR (FIG. 1). However, the degree of decrease in insulin sensitivity seen following hemorrhage (34.3%) was not compatible with the 55% reduction reported when atropine is used alone to produce full HDIR (FIG. 1). This unexpected response was clarified by examining the effect of hemorrhage on the RIST index in the absence of HISS action produced by pre-treatment with atropine.

Thus, hemorrhage caused complete HDIR and did not induce resistance to the direct action of insulin. However, the response to administered insulin was confounded by the impact of reduced hepatic blood flow on insulin metabolism that resulted in an increase in the HISS independent (direct) action of insulin. This complication is of concern only for the specific experimental protocol where exogenous insulin was administered and is not of consequence in the physiological response to hemorrhage since part of the neuroendocrine response includes the suppression of insulin secretion. In this way, the glycogenolysis, inhibition of insulin release and suppression of HISS action serve to maintain hyperglycemia following hemorrhage.

Example Two

Effect of Superior Mesenteric Artery (SMA) Occlusion and Hemorrhage on Portal Blood Flow and Insulin Pharmacokinetics SMA Occlusion: The SMA ligation was performed to determine the effect of reduced portal blood flow on insulin kinetics. A standard surgical preparation was performed, followed by a laparotomy and the isolation of the SMA. A snare was inserted around the artery, so that it could be occluded and released. An ultrasonic perivascular V-type flow probe was placed around the portal vein (size, 3 mm) to allow for the measurement of portal blood flow with a small animal flowmeter (T206, Transonic Systems Inc., Ithaca, N.Y.). Following a 30 minute stabilization period, the snare encompassing the SMA was constricted for 5 minutes. Portal blood flow, arterial pressure and glycemia were measured when the SMA was occluded. The snare was released, and following restabilization, a hemorrhage was performed as above. Portal blood flow, arterial pressure and glycemia were measured when arterial pressure was reduced to 50 mmHg and held for 10 minutes.

Figure 2:
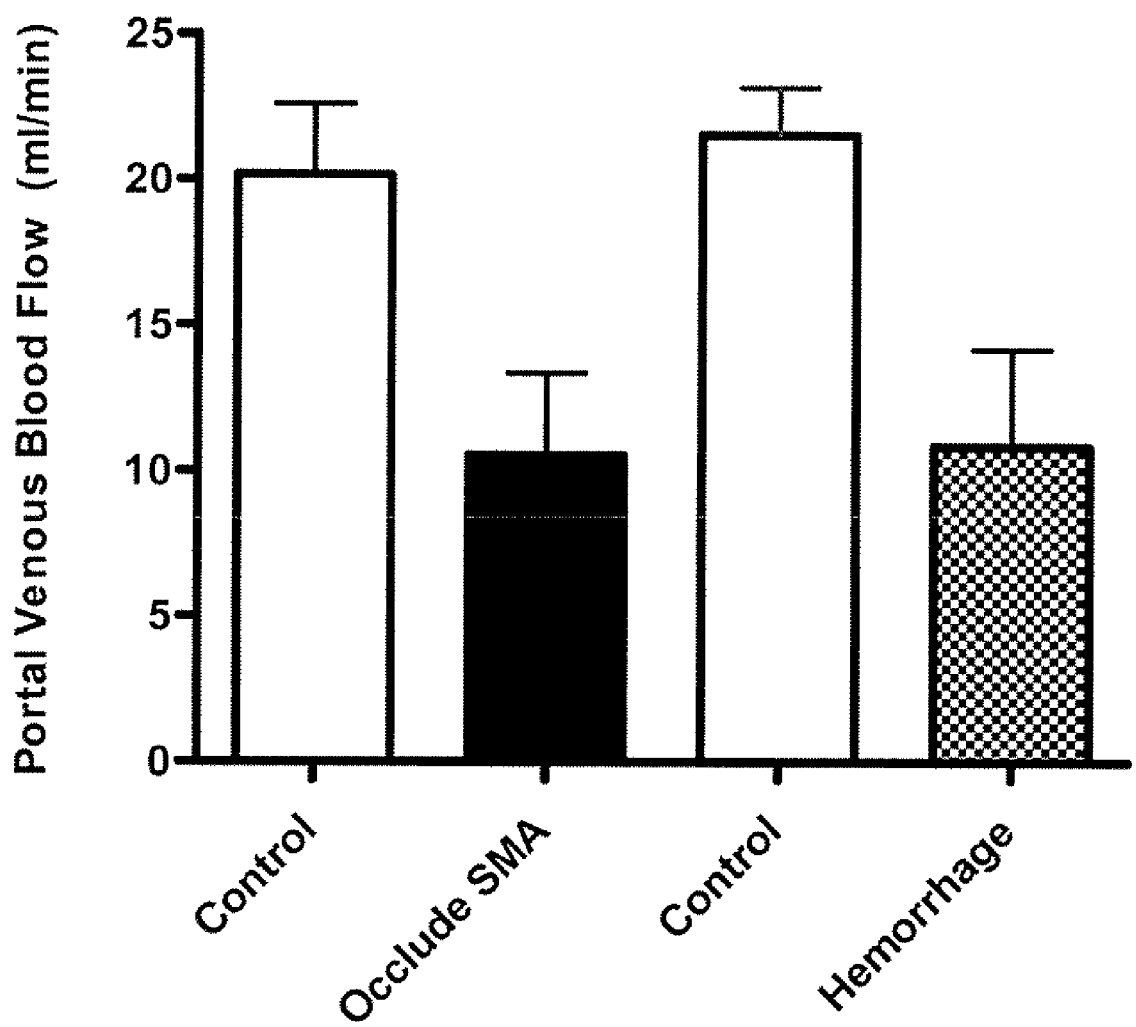
FIG. 2 is a bar graph comparing the effect of superior mesenteric artery (SMA) occlusion and hemorrhage on portal blood flow.

Results: Animals in this series (n=3; 277.6±9.9 grams) were used to determine portal blood flow rates following SMA occlusion and hemorrhage. The amount of time taken to remove the Volume of blood (3.5±1.1 ml) required to reduce mean arterial pressure to 50 mmHg was 4.9±0.8 minutes. Hyperglycemia was immediately present as basal glucose levels increased from a baseline of 106.6±5.2 to 129.0±4.4 mg/dl within 5 minutes of onset of hemorrhage. There was a 51.0±1.2% reduction in portal blood flow after SMA occlusion, and a 49.7±2.4% reduction in flow after hemorrhage, with mean occlusion flow rates being 10.5±2.8 and mean post hemorrhage flow rates equaling 10.8±3.3 ml/min (FIG. 2). Hemorrhage significantly reduced portal blood flow to the same extent as SMA occlusion, thereby facilitating comparison of altered insulin pharmacokinetics attributable to altered portal flow during hemorrhage.

Hemorrhage and Insulin Pharmacokinetics: For pharmacokinetic studies, insulin was administered for the RIST at the standard dose (50 mU/kg) but over a 30 second interval. Following the hemorrhage, another RIST was performed. Blood samples (80 μL) were taken from the arterial side of the shunt at 5 minutes before beginning the RIST, 1, 2, 3, and 5 minutes after insulin administration. The samples were centrifuged and the plasma was frozen immediately on dry ice, and stored at −80° C. These samples were analyzed in duplicate on a 1-2-3 Ultra Sensitive Rat Insulin ELISA (American Laboratory Products Company, Windham, N.H.).

Figure 3:
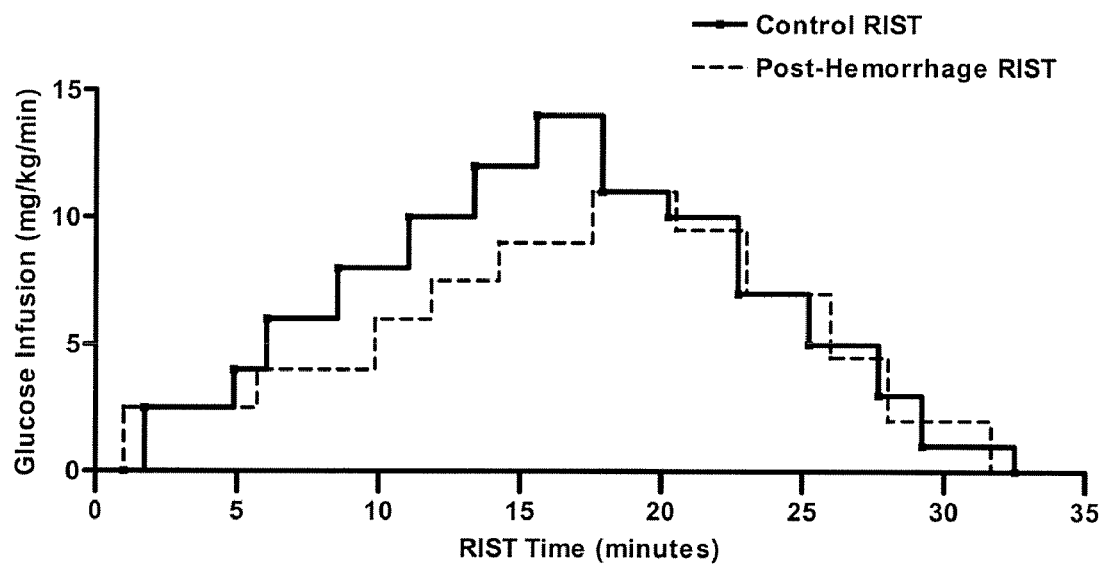
FIG. 3 comprises line graphs illustrating the effect of hemorrhage on the RIST index (top panel) and on the clearance of insulin (bottom panel).
Figure 3:
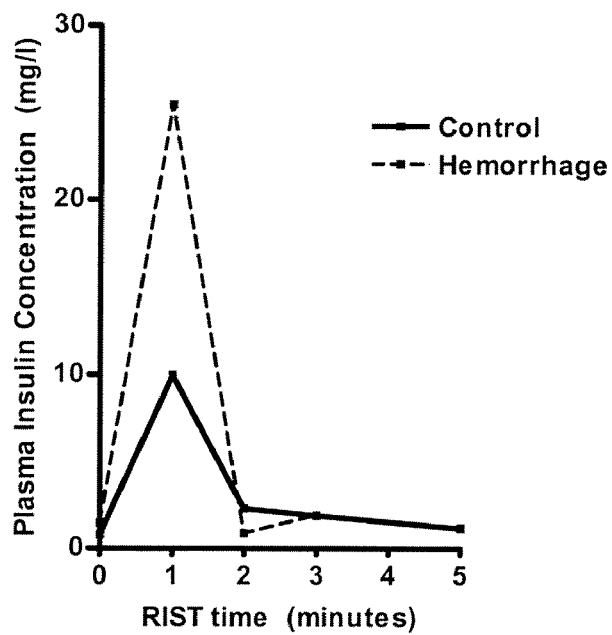

Results: Animals (n=4; 265.8±1.9 grams) in this series were used to analyze insulin kinetics during the RIST following hemorrhage. FIG. 3 shows the impact of hemorrhage after administration of a 30 second bolus of 50 mU/kg of insulin on insulin kinetics and the dynamic curve of the RIST index in one typical experiment. Insulin decreased to baseline after 5 minutes in both the control and hemorrhage RISTs. The hemodynamic alteration by hemorrhage caused an increase in insulin concentration following hemorrhage, and the area under the curve for insulin concentration was increased secondary to reduced volume of distribution and clearance (n=4, see Table 1 and text for mean data). Despite the increased availability of insulin to act on tissues, the response to insulin decreased because of the absence of HISS action.

The control RIST index decreased from 211.8±15.8 by 33.1±4.4% after hemorrhage to 141.8±9.6 mg of glucose/kg (P=0.0021). The time to remove the volume of blood (3.0±0.9 ml) required to reduce mean arterial pressure to 50 mmHg was 4.3±0.6 minutes. Glucose levels increased from a mean baseline of 110.5±4.1 to 126.9±5.4 mg/dl within 5 minutes of onset of hemorrhage. A partial restoration (50.0±0.0 to 59.8±1.9 mmHg) of mean arterial pressure following hemorrhage occurred prior to stabilization of arterial glucose levels and the post hemorrhage RIST. Hemorrhage caused a significant increase in insulin concentration (27.5±3.8 μg/l) at the 1 minute mark of the RIST, as compared to the control state (17.5±1.8 μg/l) (P=0.03). The area under the curve for insulin concentration was increased by 35.0±2.1% secondary to reduced volume of distribution and clearance (Table 1). Therefore, during the RIST, more insulin is available to interact with tissues following hemorrhage (FIG. 3).

TABLE 1

Insulin Kinetics from the Hemorrhage and Superior Mesenteric Artery (SMA) ligation series.

| Intervention | | Volume of Distribution (ml/kg) | Clearance (ml/kg/hr) |
| --- | --- | --- | --- |
| Hemorrhage | Control | 56.0 ± 12.0 | 62.0 ± 9.0 |
| | Hemorrhage | 24.0 ± 7.0 | 34.0 ± 5.0 |
| | Percent Change | 57.14% | 45.16% |
| SMA Ligation | Control | 98.0 ± 14.0 | 87.0 ± 1.8 |
| | SMA Ligation | 30.0 ± 3.0 | 40.0 ± 1.0 |
| | Percent Change | 69.39% | 54.02% |

Data (mean±SE) were collected during the hemorrhage and SMA occlusion protocols. Hemorrhage and SMA ligation interventions reduced hepatic portal blood flow to similar extents. The volume of distribution and the clearance rates were not found to be statistically significantly different.

SMA Occlusion and Insulin Pharmacokinetics: To study the effect of SMA occlusion on insulin pharmacokinetics, a standard surgical preparation was performed, followed by a laparotomy and the isolation of the SMA. A snare was inserted around the artery so that it could be occluded. The animal was allowed to rest for a 30 minute interval. Atropine was administered (1 mg/kg IV) followed by a 15 minute stabilization period. A post atropine RIST was then performed as described above for insulin kinetic determination. The SMA was then occluded, the animal was restabilized, and a RIST was repeated to determine insulin pharmacokinetics. The samples collected were analyzed using the above methods for insulin pharmacokinetic determination.

Figure 4:
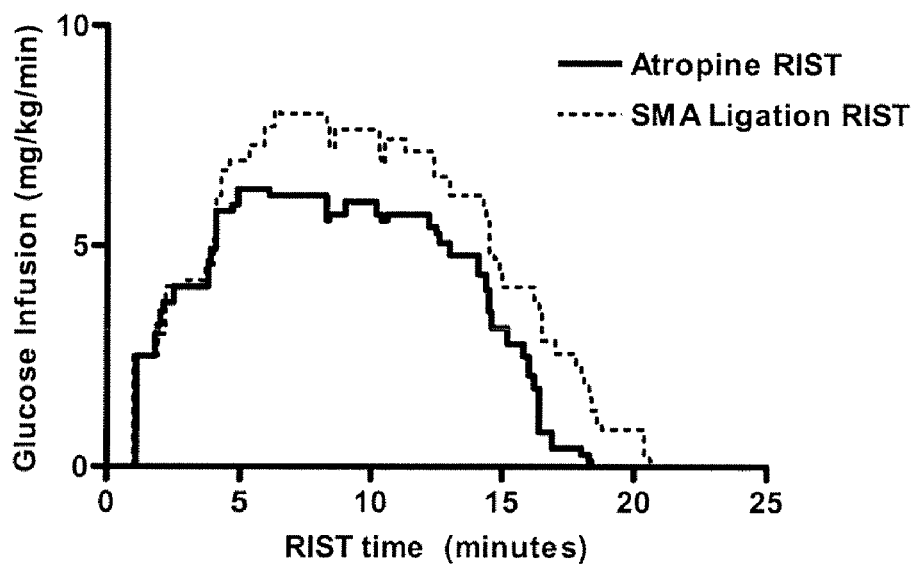
FIG. 4 comprises line graphs illustrating the effect of SMA occlusion on the RIST index (top panel) and on the clearance of insulin (bottom panel).
Figure 4:
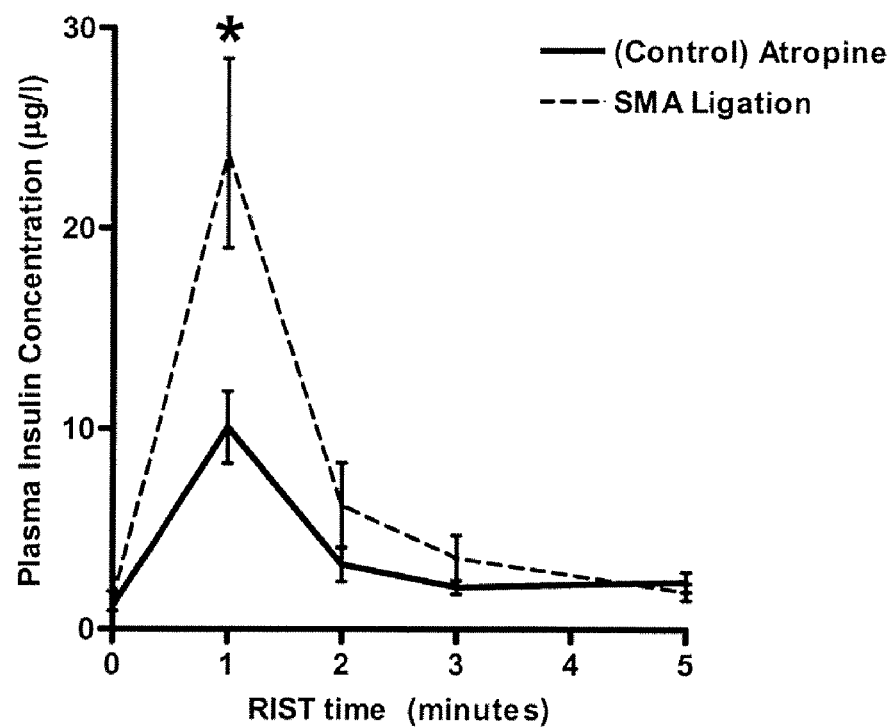

Results: Animals (n=7; 290.0±10.0 grams) in this series were used to determine insulin kinetics and insulin sensitivity during SMA occlusion. Atropine (1 mg/kg-IV) was administered prior to the control RIST in order to eliminate HISS so that alterations in insulin kinetics and the RIST index could be interpreted as due only to the direct effect of insulin. FIG. 4 shows the impact of superior mesenteric artery (SMA) ligation after administration of a 30 second bolus of 50 mU/kg of insulin on insulin kinetics and the dynamic curve of the RIST index. Atropine was administered prior to the control RIST to completely block HISS release, so that only the impact of insulin action was measured. The post ligation RIST is significantly higher (***P=0.0006) than the control post atropine RIST, consistent with the altered insulin kinetics (FIG. 4, Table 1).

The SMA occlusion caused a significant increase (24.4±2.6%) in insulin sensitivity, as the post atropine control RIST index was 77.0±1.7, and the occlusion RIST index was 101.9±11.3 mg of glucose/kg (P=0.0006, FIG. 4). In addition, the SMA occlusion altered insulin kinetics thereby increasing the area under the insulin concentration curve (55.2±3.2%, *P=0.047) secondary to reduced volume of distribution and clearance (FIG. 4, Table 1). This allowed for a higher insulin concentration to interact with tissues leading to an increase in the RIST index altered during SMA occlusion.

Discussion: The reduction in hepatic portal blood flow caused by hemorrhage and SMA occlusion was used to investigate effects on insulin kinetics. The insulin kinetic studies were analyzed using a one compartment model, with zero order infusion and first order elimination.

Insulin administered during the RIST is rapidly equilibrated and distributed among the tissues and body fluids. It is then cleared mainly by the liver and kidneys. The hepatic clearance of many compounds is blood-flow dependent. The SMA contributes a major component of portal blood flow. It was hypothesized that hemorrhaging an animal to an arterial pressure of 50 mg would closely mimic the hemodynamic effect of a SMA occlusion on hepatic portal flow. Hemorrhage did mimic the occlusion as both interventions reduced portal flow by approximately 50% in rats (FIG. 2).

Although the RIST is usually done using a 5 minute infusion, there is no substantive difference in the RIST index or profile if the same dose is given over 30 seconds in rats (Lautt W W, Wang X, Sadri P, Legare D J, and Macedo M P. Rapid insulin sensitivity test (RIST). *Can J Physiol Pharmacol* 76: 1080-1086, 1998). In order to do insulin kinetics we used the 30 second bolus administration. The RIST index (204.8±11.3) using the 5 minute bolus and the RIST index (211.8±15.8 mg of glucose/kg) for the 30 second bolus were not statistically different. Thus the RIST index was analogous using the 5 minute or 30 second insulin infusion.

While the hemorrhage reduced portal blood flow to a level equivalent to the SMA occlusion, the ligation produced a larger reduction (69.4±2.2%) in the apparent volume of distribution primarily because of the static exclusion of a large portion of the gastrointestinal tract from the circulation (FIG. 4, Table 1). The hemorrhage intervention caused a smaller reduction in the apparent volume of distribution (57.1±4.0%) (FIG. 3). Although blood volume was physically removed from the anaesthetized animal during the hemorrhage, the gastrointestinal circulation would have been reduced but not completely stagnant. The clearance of insulin from the plasma was decreased by 54.0±1.9% in the ligation study and by 45.2±3.8% in the hemorrhage intervention (Table 1). The discrepancy between the clearance rates may be accounted for by the fact that a time delay (35±4.9 minutes) subsequent to the hemorrhage intervention allowed for the gradual increase of hepatic blood flow as compared to the SMA ligation which was held steady. This partial restoration of hepatic blood flow was consistent with the increase in mean arterial pressure from 50.0±0.0 to 62.4±2.0 mmHg following hemorrhage. These data support the hypothesis that although full HDIR occurred in response to hemorrhage, the reduced hepatic blood flow led to reduced insulin clearance so that the direct effect of injected insulin was increased thus accounting for hemorrhage reducing the RIST index by only 34.3% versus the anticipated 55%.

The reduction in hepatic portal venous flow by 49.7±2.4% following hemorrhage was associated with a reduction in insulin clearance by 45.2±3.8%. Most likely, the total reduction in clearance can be explained by the reduction in portal flow without compensatory changes to the extraction ratio. Insulin has a reported hepatic extraction ratio of 19% in the rat at 3 hours and 24 hours after feeding (Messerli F H, Nowaczynski W, Honda M, Genest J, Boucher R, Kuthel O, and Rojo-Ortega J M. Effects of angiotensin II on steroid metabolism and hepatic blood flow in man. *Circ Res* 40: 204-207, 1997). A reduction in portal flow would, according to clinical pharmacokinetic theory (Branch R A, Shand D G, Wilkinson G R, and Nies A S. The reduction of lidocaine clearance by dl-propranolol: an example of hemodynamic drug interaction. *J Pharmacol Exp Ther* 184: 515-519, 1973), be expected to lead to an increased extraction ratio and a modest reduction in clearance. Drugs or hormones that have high extraction ratios are expected to have blood flow dependent clearance, while compounds with low extraction ratios are expected to have little flow dependence for clearance. Discrepancy with this theory has previously been reported for lidocaine clearance in cats, where the extraction ratio of 30% was not altered by reduced flow, thereby making clearance directly related to hepatic blood flow (Lautt W W and Skelton F S. The effect of SKf-525A and of altered hepatic blood flow in lidocaine clearance in the cat. *Can J Physiol Pharmacol* 55: 7-12, 1977). Hormones which have hepatic flow dependent clearance include aldosterone, cortisol, and progesterone (Yates F E. Contributions of the liver to steady-state performance and transient responses of the adrenal cortical system. *Fed Proc* 24: 723-730, 1965), to which insulin can be added.

Example Three

Effect of Hemorrhage on Insulin Resistance in Rats Pre-Treated with Atropine

A control RIST was performed after a 30 minute stabilization period. This was followed by administration of atropine (1 mg/kg IV). A post atropine RIST was done followed by hemorrhage to 50 mmHg. A post hemorrhage RIST was then done as soon as a stable glycemic baseline had been established.

Figure 5:
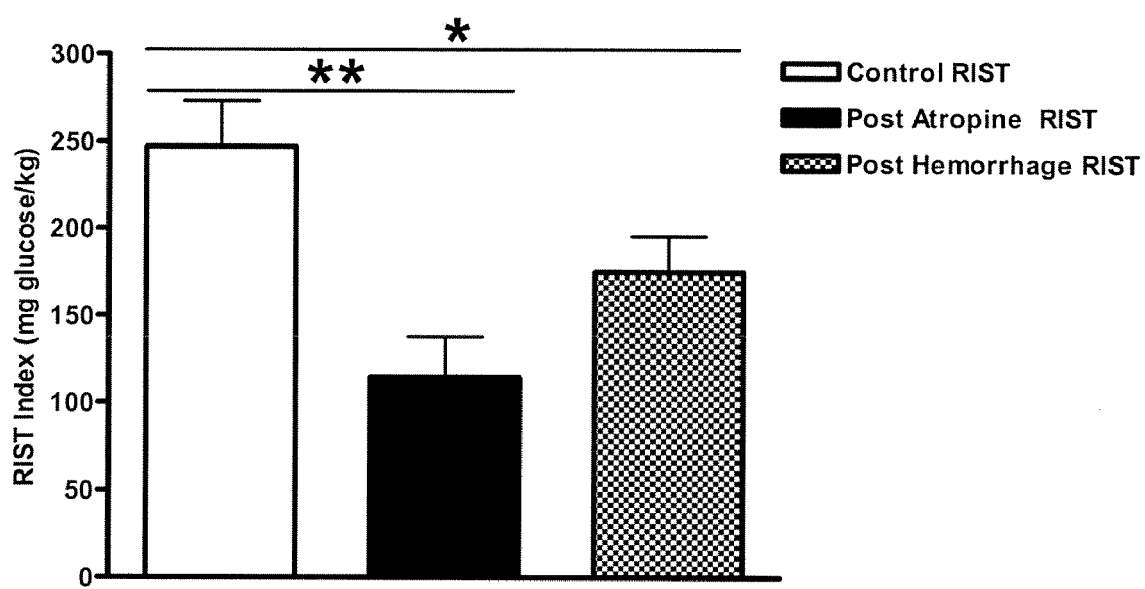
FIG. 5 is a bar graph comparing the effect of atropine pre-treatment and hemorrhage on the RIST index.

Results: To confirm that hemorrhage led to increased HISS-independent insulin action, a control RIST was performed, then HISS production blocked using atropine and then another RIST performed. The animal was then hemorrhaged and a post-hemorrhage RIST was done. FIG. 5 shows the effect of hemorrhage on HISS-dependent insulin resistance when pre-treated with atropine. The post atropine RIST index was due entirely to the direct action of insulin (HISS-independent component) and was significantly elevated following hemorrhage because of altered insulin kinetics secondary to reduced volume of distribution and clearance (**P=0.023, *P=0.041) (Table 1).

Animals (n=4; 253.1±8.1 grams) in this series had an initial RIST index of 247.1±26.1, a post atropine RIST index of 114.6±23.1 and a post hemorrhage RIST index of 175.0±20.7 mg of glucose/kg (FIG. 5). The time taken to remove the volume of blood (3.4±0.5 ml) required to in reduce mean arterial pressure to 50 mmHg was 4.1±0.9 minutes. Basal glucose levels rose from a mean baseline of 108.8±7.1 to 131.1±3.3 mg/dl within 5 minutes of onset of hemorrhage. A partial restoration (50.0±0.0 to 60.2±1.7 mmHg) of mean arterial pressure was noted following hemorrhage prior to the third RIST. Subsequent to hemorrhage, the RIST index increased (29.1±6.1%) in comparison to the post atropine RIST. The decrease (53.6±3.0%) in insulin sensitivity following atropine administration confirms full HISS blockade (P=0.041). The post atropine RIST index was due entirely to the direct action of insulin (HISS-independent component) and was significantly elevated following hemorrhage (P=0.041).

Discussion: Atropine (1 mg/kg IV) was administered prior to the hemorrhage in order to induce HDIR, and as expected, the RIST index was reduced by 53.6±3.0% (FIG. 5). However, subsequent to hemorrhage, the RIST index increased by 29.1±6.1% in comparison to the post atropine RIST. As the only contribution to the RIST index was insulin, this response suggested that hepatic clearance of the injected insulin had been reduced secondary to the decrease in hepatic blood flow that occurred in response to hemorrhage.

Example Four

Somatostatin Causes HDIR

Effect of Somatostatin on RIST Index: A standard surgical preparation, laparotomy and portal puncture were performed. A control RIST was performed after a 30-minute stabilization period. Subsequent to continuous somatostatin (0.16 µg/kg/min-IV) infusion at a rate of 0.025 ml/min, the animal was stabilized, and a RIST was completed. Immediately following the RIST, somatostatin administration was discontinued and the animal was allowed to restabilize for 50 minutes after which a RIST was performed to determine the reversibility of HDIR caused by somatostatin.

Figure 6:
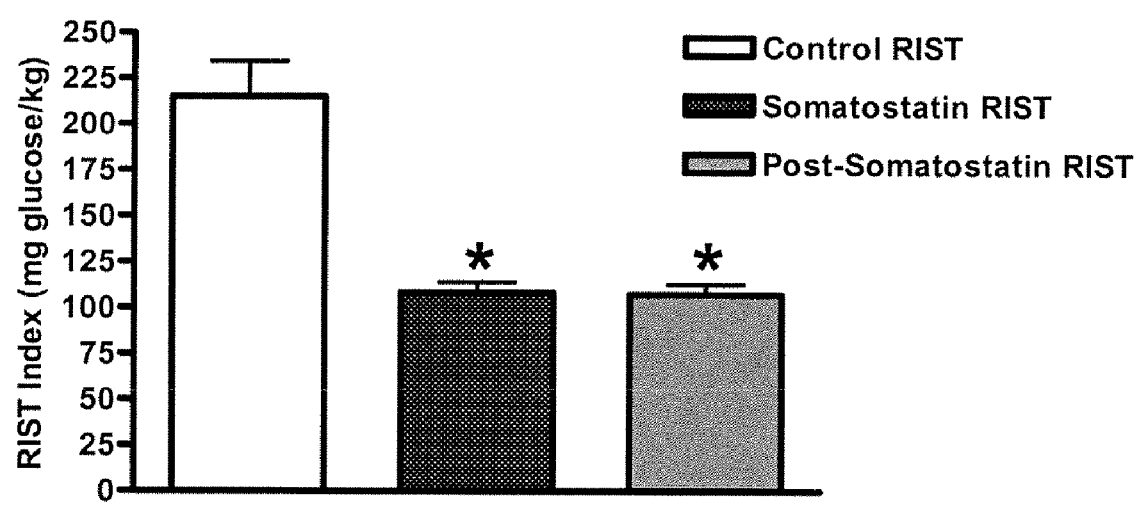
FIG. 6 is bar graph illustrating the effect of somatostatin on the RIST index.

Results: Animals (n=4; 278.0±13.9 grams) in this series were used to analyze the effects of somatostatin (0.16 µg/kg/min-IPV) on the RIST index. FIG. 6 shows the effect of somatostatin on the RIST index following administration and subsequent to ceasing infusion. The RIST index with the somatostatin infusion significantly (*,P=0.0002) decreased by 49.6%. The somatostatin infusion (0.16 µg/kg/min-IPV) was turned off and the animal was restabilized for 50 minutes. The somatostatin infusion had no effect on glycemic levels during its continuous infusion as the glycemic baseline for the control (108.0±3.5 mg/dl), somatostatin (106.2±4.1 mg/dl), and post-somatostatin (109.3±2.4 mg/dl) RISTs were not significantly different. The control RIST index was 215.0±19.2 and the somatostatin RIST index was 108.4±5.6 mg of glucose/kg. The decrease (49.6±5.8%) in insulin sensitivity between the control and somatostatin RIST is significant (P=0.0002). The post-somatostatin RIST index (107.3±5.5 mg of glucose/kg) was not significantly different from the somatostatin RIST index, which occurred 50 minutes following the discontinuation of somatostatin infusion.

Effect of Somatostatin on HDIR: A standard surgical preparation, laparotomy and portal puncture was performed. After a control RIST was completed, somatostatin (0.16 µg/kg/min-IV) was continuously administered as above and a somatostatin RIST was done. Immediately following the RIST, somatostatin administration was discontinued, and atropine was administered (1 mg/kg-IV). A post atropine RIST was then done to determine the extent of HDIR produced by somatostatin.

Figure 7:
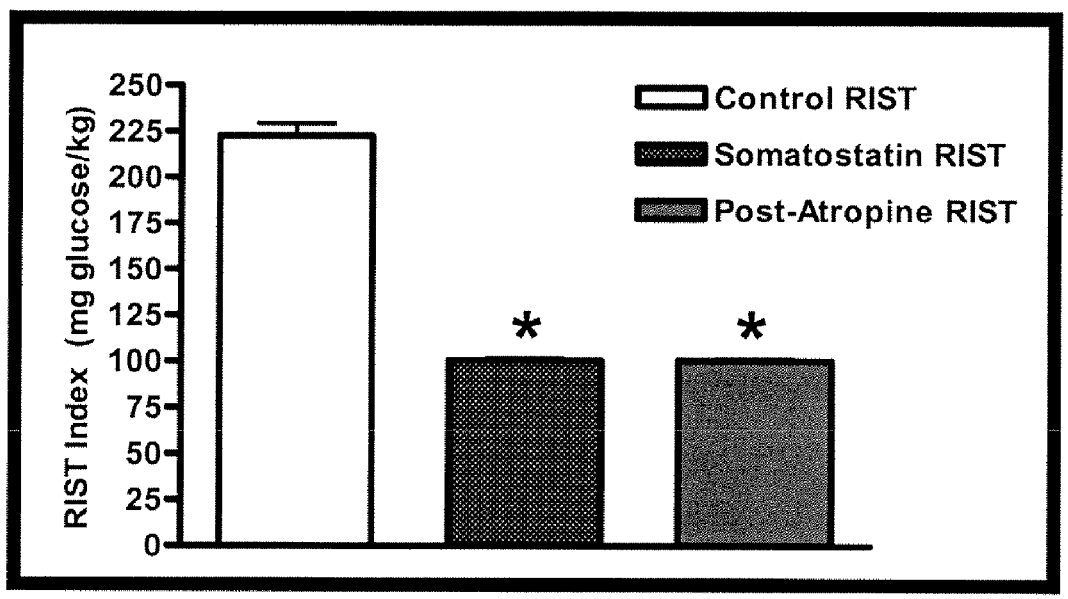
FIG. 7 is a bar graph comparing the effect of somatostatin and somatostatin followed by atropine on the RIST index.

Results: Animals in this series (n=3; 269.5±2.5 grams) were used to illustrate that somatostatin (0.16 µg/kg/min-IPV) administration causes a reduction (54.9±1.2%) in the RIST index that was not reduced further by atropine administration (1 mg/kg-IV). FIG. 7 shows that somatostatin resulted in HISS-dependent insulin resistance as confirmed by a post-atropine test. The RIST index with the somatostatin infusion (0.16 µg/kg/min-IPV) decreased (*,P=0.0003) by 54.90% and was not decreased further by the administration of atropine (1 mg/kg-IV). Somatostatin caused complete HISS-dependent insulin resistance.

The control RIST index was 222.7±6.5, the somatostatin RIST index was 100.5±1.3 and the post atropine RIST index was 100.5±0.9 mg of glucose/kg. The 54.9% reduction in the RIST index in both the somatostatin and atropine interventions confirms full HISS blockade (P=0.0003), thus demonstrating the presence of insulin action only.

Discussion: Exogenous somatostatin (0.16 µg/kg/min) caused a reduction (49.6%) in insulin sensitivity that was identifiable using RIST methodology (FIG. 6). Following the termination of a continuous somatostatin infusion, and after a 50 minute stabilization period, it was evident that the reduction in insulin sensitivity was not reversible, even though the half-life of somatostatin is approximated at 1.5 minutes (Shen, L. P., Pictet, R. L., Rutter, W. J. Human somatostatin I: Sequence of the cDNA. Proc Natl Acad Sci USA 79:4575-9, 1982). In order to decipher if the reduction in insulin sensitivity seen during somatostatin administration was attributable to the absence of HISS, a subsequent study was performed with atropine, which is known to block HISS release (Takayama, W., Legare, D. J., Lautt, W. W. Dose-related atropine-induced insulin resistance: comparing intraportal versus intravenous administration. Proc. West. Pharamcol. Soc. 43:33-34, 2000). Following the completion of this series, it was concluded that the reduction in insulin sensitivity seen during somatostatin infusion was complete HDIR, as the atropine intervention illustrated no further reduction in the RIST index (FIG. 7). Therefore, somatostatin demonstrated insulin resistance that was accountable by HDIR with direct HISS-independent action being unsuppressed.

Example Five

Endogenous Somatostatin Levels Following Hemorrhage

Following standard surgical preparation, and 30 minute recovery time, the first baseline blood sample of 120 µL was taken and treated as above. Following the initial sample, the animal was hemorrhaged to 50 mmHg from the shunt. The second blood sample was taken at the instant that arterial pressure had been reduced to 50 mm Hg. The third sample was taken 10 minutes later. The animal was then stabilized for 100 minutes, with 2 more samples being taken 50 minutes apart during this period. The volume of blood taken from the animal (120 µL×3=360 µL) prior and subsequent to hemorrhage was counted towards the total volume required to reduce the animal's arterial blood pressure to 50 mmHg.

Figure 9:
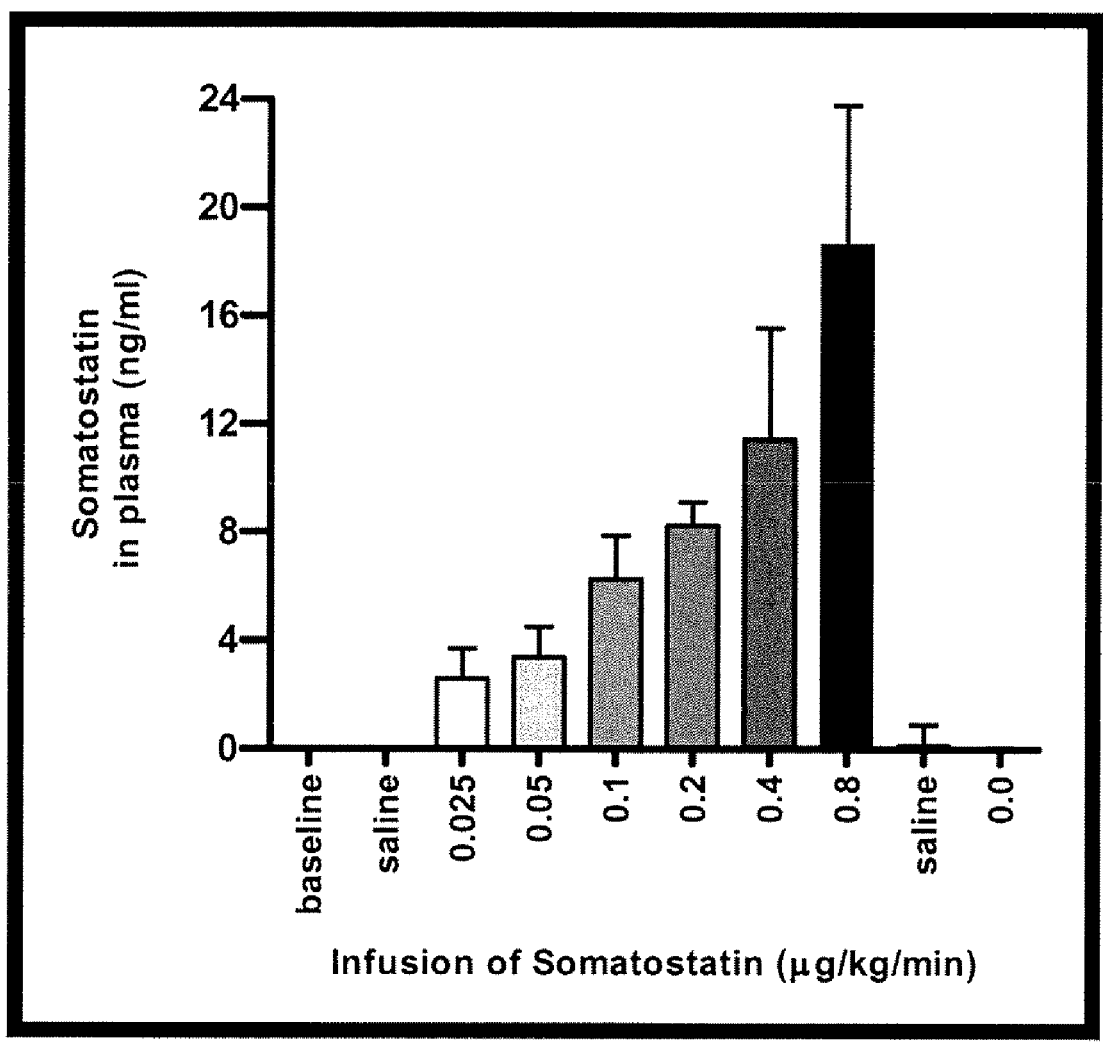
FIG. 9 is a bar graph comparing the plasma somatostatin concentration in rat following differing administered doses of somatostatin.

Results: Animals (n=3; 287.1±6.0 grams) were used to create a dose concentration curve. The infusions of somatostatin (saline, 0.025, 0.05, 0.1, 0.2, 0.8 µg/kg/min) were administered for 10 minutes to ensure that steady state had been reached. FIG. 9 shows the plasma somatostatin concentration in the rat following differing administered doses of somatostatin. Somatostatin was detected in the plasma by a peptide enzyme immunoassay. The assay was able to sensitively distinguish the increasing concentration of the somatostatin doses administered.

The assay was capable of measuring exogenous somatostatin administered in the plasma, therefore this assay was used to measure endogenous somatostatin released following acute hemorrhage. The baseline samples read as 0.011±0.004, the samples taken when mean arterial pressure had been reduced to 50% were 0.017±0.009, the samples taken at the 10 minute period after hemorrhage was complete were 0.022±0.002, the samples taken 60 minutes subsequent to hemorrhage discontinuation were 0.009±0.002, and lastly samples collected at 110 minutes after hemorrhage were 0.025±0.007 ng/ml. The time points selected were able to detect somatostatin but only small increments, and in sporadic patterns that were not statistically significant.

Discussion: As stated previously, the rapid release of somatostatin following hemorrhage has been observed in cats (Lautt, W. W., Dwan, P. D., Singh, R. R. Control of the hyperglycemic response to hemorrhage to cats. *Can J Physiol Pharmacol*. 60: 1618-1623, 1982). Insulin levels are dramatically decreased during shock and trauma in several species including man (Hiebert, J. M., J. M. McCormick, R. H. Egdahl. Direct measurement of insulin secretory rate: studies in shocked primates and postoperative patients. *Ann. Surg:* 176:296-304,1972. Hiebert, J. M., C. Kieler, J. SSS. Soldner, R. H Egdahl. Species differences in insulin secretory response during hemorrhagic shock. *Surgery:* 79:451-455, 1976) following stress-induced hyperglycemia. Therefore, the release of excess somatostatin during a period of traumatic stress is beneficial, as reductions in insulin and HISS levels allow for the utilization of glucose for life-sustaining systems and for the osmotic pressure-induced mobilization of extravascular fluid into the circulation (Yamaguchi, N. Sympathoadrenal system in neuroendocrine control of glucose: mechanisms involved in the liver, pancreas, and adrenal gland under hemorrhagic and hypoglycemic stress. *Can J Physiol Pharmacol*. 70(2):167-206, 1992). However, there appears to be significant species differences between the cat and rat, as systemic endogenous somatostatin levels were not elevated and were only present in small, sporadic amounts following hemorrhage in the rat. Given that HDIR subsequent to hemorrhage is mediated by endogenous somatostatin, the lack of increase in circulating plasma somatostatin levels suggests that the somatostatin of relevance to HDIR is released from within the liver and that circulating systemic levels of somatostatin does not play a role in the rat.

Example Six

Cyclosomatostatin Prevents Somatostatin-Induced HDIR

A standard surgical preparation, laparotomy and portal puncture was performed. After a control RIST was completed, cyclosomatostatin (20 µg/kg/min-IPV) infusion was initiated. 10 minutes after the initiation of cyclosomatostatin infusion, somatostatin (0.16 µg/kg/min-IV) was continuously administered. Glycemia was monitored until a stable baseline was established, and a RIST was performed during the continuous infusion of both cyclosomatostatin and somatostatin. Following completion of the RIST, the cyclosomatostatin infusion was terminated, and the somatostatin infusion remained on. A RIST was repeated. Atropine (1 mg/kg-IV) was then administered, and a post atropine RIST was performed to determine the extent of HDIR produced by somatostatin. Pilot studies indicated that a dose of 10 µg/kg/min of cyclosomatostatin did not produce a full blockade of somatostatin induced HDIR.

Figure 8:
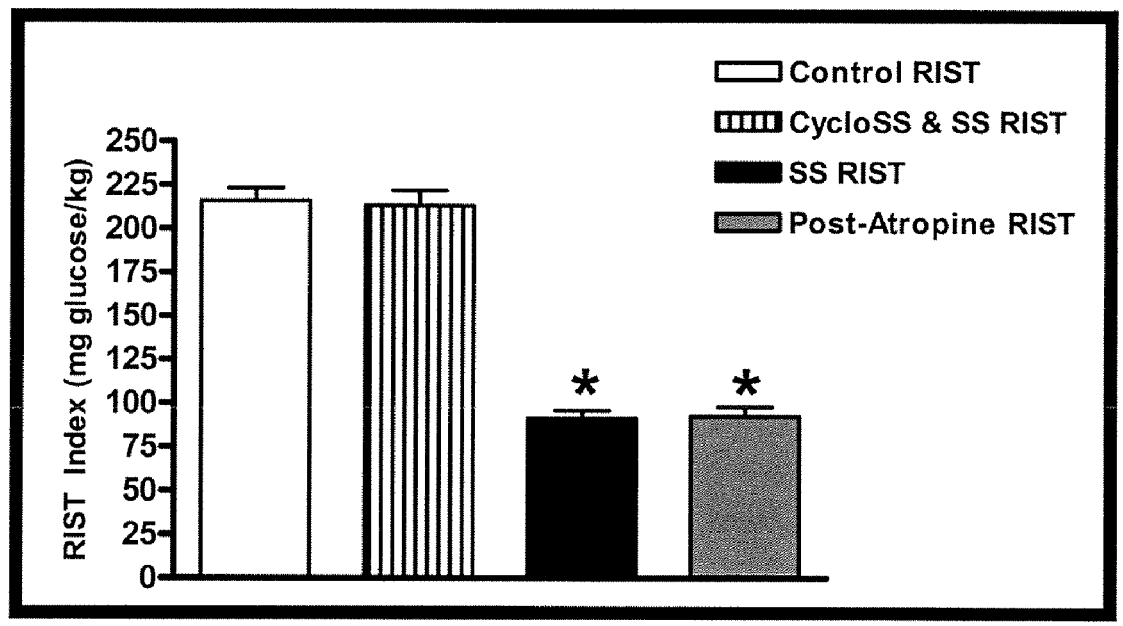
FIG. 8 is a bar graph comparing effect of somatostatin and cyclosomatostatin followed by somatostatin on the RIST index.

Results: Animals in this series (n=3; 274.9±4.8 grams) were used to illustrate that the continuous infusion of cyclosomatostatin (20 µg/kg/min-IPV) significantly prevented the occurrence of HDIR (P=0.0001). FIG. 8 shows that cyclosomatostatin administered prior to somatostatin prevents the occurrence of HDIR. There was no significant difference between the control and cyclosomatostatin (cycloSS) and somatostatin (SS) RIST index, thereby indicating that HDIR was prevented. The RIST index with the somatostatin infusion (0.16 µg/kg/min-IPV) decreased (*,P=0.0001) by 57.1% and was not decreased further by the administration of atropine (1 mg/kg-IV).

The control RIST index was 215.9±7.4, the cyclosomatostatin and somatostatin RIST index was 213.1±8.6, the somatostatin RIST index was 91.1±4.7, and the post atropine RIST index was 92.7±5.2 mg of glucose/kg. Cyclosomatostatin was continuously administered for 58.1±7.6 minutes, and somatostatin was continuously infused for 87.8±5.5 minutes, and neither drug had a significant effect on glycemic levels. HDIR was produced with both the atropine (1 mg/kg) and somatostatin (0.16 µg/kg/min-IV) interventions (FIG. 8), as shown by the inability of atropine to cause a further reduction in the RIST index. There were no significant differences between the somatostatin and post-atropine RIST. The 57.1±1.4% reduction in the RIST index in both the somatostatin and atropine interventions confirms full HISS blockade (P=0.0001), thus demonstrating the presence of insulin action only.

Discussion: In order to determine if the blockade of HISS action following somatostatin-induced HDIR could be prevented, a somatostatin antagonist (cyclosomatostatin) was employed. Cyclosomatostatin (20 µg/kg/min) prevented the blockade of HISS (FIG. 8) when it was administered concurrently with somatostatin (0.16 µg/kg/min). In order to demonstrate that HISS action could be blocked in this study, an atropine intervention confirmed complete HDIR as indicated by a 57.1% reduction in the RIST index. Therefore, the dose of 20 µg/kg/min of cyclosomatostatin prevented somatostatin-induced HDIR.

Example Seven

Alpha-Adrenergic Blockade does not Prevent Hemorrhage-Induced HDIR

Effect of Phentolamine on HDIR following Hemorrhage: Following a standard surgical preparation, a laparotomy and portal puncture was performed. After a 30 minute stabilization period, a control RIST was performed. Following the RIST, phentolamine (400 µg/kg/min-IPV, 10 minute infusion at a rate of 0.025 ml/min), or cyclosomatostatin (20 µg/kg/min-IPV, continuous infusion at a rate of 0.025 ml/min) was administered. The rat was restabilized and then hemorrhaged to an arterial blood pressure of 50 mmHg and held at this pressure for a ten-minute interval. Glycemic levels were closely monitored during and after hemorrhage, until they became stable for at least 15 minutes. A post-hemorrhage RIST was performed. When the cyclosomatostatin series was attempted, the cyclosomatostatin infusion was ceased immediately following the post hemorrhage RIST, and atropine was administered (1 mg/kg-IV). The animal was stabilized and a post-atropine RIST was performed.

Figure 10:
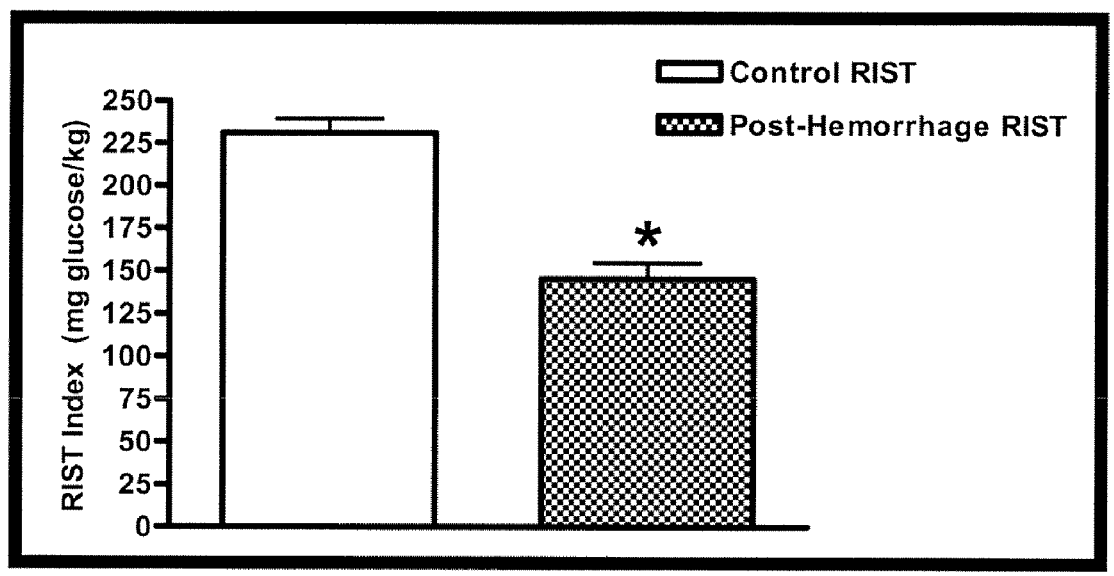
FIG. 10 is a bar graph illustrating the effect of phentolamine on hemorrhage induced reduction in the RIST index.

Results: Animals (n=7; 293.7±5.0 grams) in this series were used to analyze the effects of phentolamine on HDIR. FIG. 10 shows that HDIR induced by hemorrhage after alpha adrenergic receptor blockade. The post-hemorrhage RIST was significantly different (*,P=0.0001) from the control RIST. The decline in the RIST index (31.8%) is similar to the reduction seen when atropine induced full HDIR. Phentolamine (400 µg/kg-IPV) was unable to prevent the reduction in the RIST index from occurring post hemorrhage.

The control RIST index was 213.1±8.4 and the post hemorrhage RIST index was 145.4±9.2 mg of glucose/kg. Phentolamine (400 µg/kg/min-IPV) was administered at 15.1±2.2 minutes following the control RIST, prior to hemorrhage. The decrease (31.8±5.5%) in insulin sensitivity between the control and post hemorrhage RIST is significant (P=0.0001). It was previously shown that glycemia increased by 18.2±4.2% during hemorrhage (completed with no pharmaceutical agents), while phentolamine administered prior to hemorrhage diminished this effect significantly (1.1±0.9%) (P=0.0001). The impediment of hyperglycemia was indicative of a complete block of hepatic alpha-adrenergic receptors. Therefore, it was concluded that phentolamine was unable to prevent HDIR from occurring subsequent to hemorrhage.

Discussion: Phentolamine is a non-selective $\alpha_1$ and $\alpha_2$ adrenergic blocker, and can prevent α-adrenoreceptor activation during sympathetic innervation. Given that the hyperglycemia exhibited during acute blood loss is mediated primarily through the activation of alpha-2 adrenergic hepatic receptors (Kobayashi, S., Kohei, H. Some metabolic actions of imidazoline sympathomimetics: hyperglycemia and lipid mobilization J. Pharmacol. 22(Suppl):66, 1972), a sufficient dose of an α-adrenergic antagonist would terminate the response. When phentolamine (400 µg/kg/min) was administered prior to hemorrhage, the hyperglycemic response that was observed after 5 minutes was virtually abolished (only a 1.1% increase in glycemic levels). Therefore, the dose of phentolamine administered through the hepatic vein was sufficient to block hepatic α-adrenergic receptors.

Although phentolamine blocked hepatic α-adrenergic receptors, the hemorrhage intervention still produced a significant reduction (31.8%) in insulin sensitivity as measured by the RIST methodology (FIG. 10). This reduction in insulin sensitivity is similar, and not statistically different from the reduction in insulin sensitivity seen following hemorrhage alone (32.6%). As stated previously, hemorrhage results in complete HDIR, which was shown by the inability of atropine to cause a further reduction in the RIST index (FIG. 1). Therefore, it is possible to conclude that HDIR is still present during complete α-adrenergic blockade, and that α-adrenergic stimulation via the sympathetic nervous system is not directly responsible for HISS blockade following hemorrhage.

Example Eight

Beta-Adrenergic Blockade does not Prevent Hemorrhage-Induced HDIR

Identification of Blocking Dose of Isopropanol: A standard surgical preparation, laparotomy and portal vein puncture were performed on an anesthetized rat. After a 30 minute stabilization period, in which both glucose and basal heart rate readings were stable, propranolol (1.5 mg/kg-IPV) was administered at a rate of 0.1 ml/min for 5 minutes. Heart rate and glucose levels were analyzed in the last 30 seconds of propranolol administration. (Heart rate was measured using a Grass AC/DC Strain gauge amplifier and National Instrument data acquisition software.) Following stabilization, isoproterenol (0.5 µg/kg/min-IV) was administered at a rate of 0.1 ml/min for 5 minutes. Heart rate and glucose levels were analyzed in the last 30 seconds of isoproterenol administration and 15 minutes subsequent to discontinuation of isoproterenol infusion.

Results: The sole effect of isoproterenol caused an increase in basal heart rate equivalent to 125.2±9.8 beats/min while propranolol (1.5 mg/kg-IPV) caused a reduction in basal heart rate by 70.6±1.3 beats/min. When isoproterenol was administered (0.5 µg/kg/min-IV) subsequent to propranolol, the reduced heart rate increased but remained at its original baseline level (415.3±5.9 beats/min) taken before the administration of any agents. The dose of 1.5 mg/kg of propranolol was shown to completely block the acceleration in heart rate caused by isoproterenol and thus ensured the complete blockade of hepatic beta receptors.

Effect of Propanolol on HDIR following Hemorrhage: Following a standard surgical preparation, a laparotomy and portal puncture was performed. After a 30 minute stabilization period, a control RIST was performed. Following the RIST, propranolol (1.5 mg/kg-IPV, 10 minute infusion at a rate of 0.025 ml/min) or cyclosomatostatin (20 µg/kg/min-IPV, continuous infusion at a rate of 0.025 ml/min) was administered. The rat was restabilized and then hemorrhaged to an arterial blood pressure of 50 mmHg and held at this pressure for a ten-minute interval. Glycemic levels were closely monitored during and after hemorrhage, until they became stable for at least 15 minutes. A post-hemorrhage RIST was performed. When the cyclosomatostatin series was attempted, the cyclosomatostatin infusion was ceased immediately following the post hemorrhage RIST, and atropine was administered (1 mg/kg-IV). The animal was stabilized and a post-atropine RIST was performed.

Figure 11:
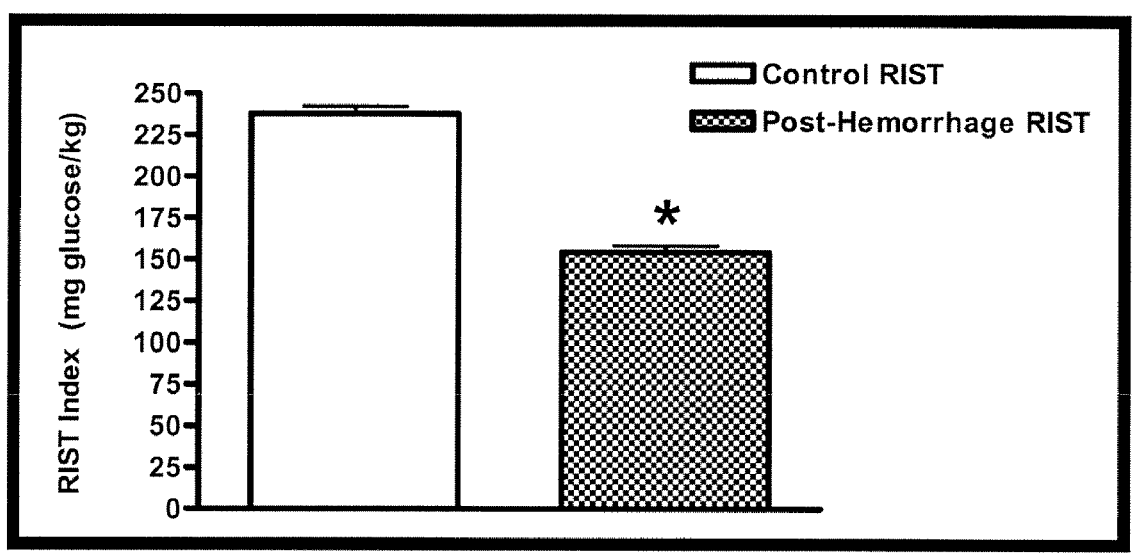
FIG. 11 is a bar graph illustrating the effect of propanolol on hemorrhage induced reduction in the RIST index.

Results: Animals (n=5; 265.4±5.8 grams) in this series were used to analyze the effects of propranolol on HDIR. FIG. 11 shows that HDIR was induced by hemorrhage after beta receptor blockade. The post-hemorrhage RIST was significantly different (*,P=0.0001) from the control RIST. The decline in the RIST index (35.1%) was similar to the reduction seen when atropine induced full HDIR.

To ensure complete blockade of hepatic beta receptors, a previously established blocking dose of propranolol (1.5 mg/kg-IPV) was administered 8.2±5.4 minutes following the control RIST, prior to hemorrhage. The control RIST index was 237.8±4.3 and the post hemorrhage RIST index was 154.4±3.9 mg of glucose/kg. The decrease (35.1±2.7%) in insulin sensitivity between the control and post hemorrhage RIST is significant (P=0.0001). Surprisingly, following hemorrhage, glycemia increased by 17.4±3.3%; thereby implying that propranolol did not alter glycemic levels significantly after hemorrhage. Therefore, propranolol was unable to prevent HDIR from occurring subsequent to hemorrhage.

Discussion: Propranolol is a non-selective $\beta_1$ and $\beta_2$ adrenergic blocker, and can prevent β-adrenoreceptor activation during sympathetic innervation when sufficiently administered. In order to ensure complete β-adrenergic blockade, heart rate was used as an indicator to assess the efficacy of the dose. Propranolol (1.5 mg/kg-IPV) completely blocked β-adrenergic receptors, as concurrent isoproterenol administration was unable to cause an acceleration in heart rate. In addition, propranolol was administered intraportally; therefore the concentration of propranolol at the hepatic receptors was substantially higher than the concentration of propranolol at the β-adrenergic receptors in the heart. The time taken to complete the hemorrhage intervention and the subsequent RIST (49.1±8.0 minutes) was a short enough time period to ensure that the hepatic beta adrenergic receptors were still blocked given that the plasma half life of propranolol is 2 hours (Tregaskis, B. F., McDevitt, D. G. Beta-adrenoceptor-blocking drugs J Cardiovasc Pharmacol. 16 Suppl 5:S25-8, 1990).

Propranolol was administered in order to block hepatic β-adrenergic receptors. Although hepatic β-adrenergic receptors were blocked, the hemorrhage intervention still produced a significant reduction (35.1%) in insulin sensitivity as measured by the RIST methodology (FIG. 11). This reduction in insulin sensitivity is similar, and not statistically different from the reduction in insulin sensitivity seen following hemorrhage alone (32.6%). Following propranolol administration (1.5 mg/kg-IPV) and the hemorrhage intervention, basal glucose levels rose by 17.4%. It was concluded that β-adrenergic stimulation in the rat does not assist in glycogenolysis during the hemorrhage intervention, as glycemia increased to a value (17.4±3.3%) that was not significantly different from the hyperglycemia exhibited during hemorrhage alone (18.2±4.2%). Therefore, it is possible to conclude that HDIR is still present during complete β-adrenergic blockade, and that β-adrenergic stimulation via the sympathetic nervous system is not directly responsible for HISS blockade following hemorrhage.

Example Nine

Cyclosomatostatin Prevents Hemorrhage-Induced HDIR

Following a standard surgical preparation, a laparotomy and portal puncture was performed. After a 30 minute stabilization period, a control RIST was performed. Following the RIST, either phentolamine (400 µg/kg/min-IPV, 10 minute infusion at a rate of 0.025 ml/min), propranolol (1.5 mg/kg-IPV, 10 minute infusion at a rate of 0.025 ml/min) or cyclosomatostatin (20 µg/kg/min-IPV, continuous infusion at a rate of 0.025 ml/min) was administered. The rat was restabilized and then hemorrhaged to an arterial blood pressure of 50 mmHg and held at this pressure for a ten-minute interval. Glycemic levels were closely monitored during and after hemorrhage, until they became stable for at least 15 minutes. A post-hemorrhage RIST was performed. When the cyclosomatostatin series was attempted, the cyclosomatostatin infusion was ceased immediately following the post hemorrhage RIST, and atropine was administered (1 mg/kg-IV). The animal was stabilized and a post-atropine RIST was performed.

Figure 12:
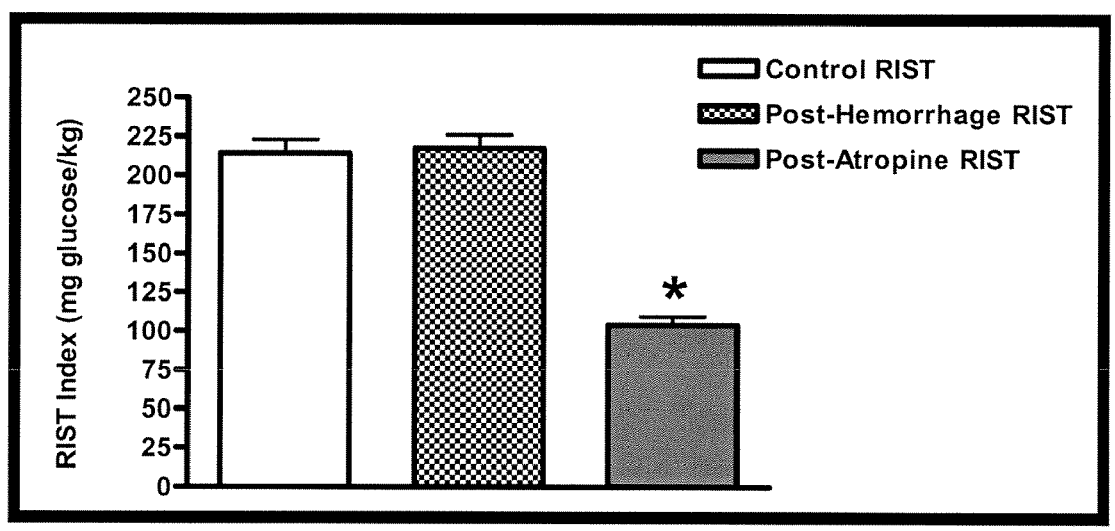
FIG. 12 is a bar graph illustrating the effect of cyclosomatostatin on hemorrhage induced reduction in the RIST index.

Results: Animals (n=5; 276.9±3.6 grams) in this series had an initial RIST index of 214.3±8.8, a post hemorrhage RIST index of 217.5±8.5 and a post atropine RIST index of 104.0±5.6 mg of glucose/kg. FIG. 12 shows that cyclosomatostatin administered prior to hemorrhage prevented the occurrence of HDIR. The administration of cyclosomatostatin (20 µg/kg/min-IPV) prior to hemorrhage is preventative as the post hemorrhage RIST was not significantly different from the control RIST (*,P=0.0001). The post atropine RIST was decreased by 52.2% illustrating complete HDIR.

The decrease (52.2±5.1%) in insulin sensitivity between the post hemorrhage RIST and the post atropine RIST is significant (P=0.0001). Cyclosomatostatin (20 µg/kg/min-IPV) was allowed to reach steady state by infusing for 10 minutes prior to hemorrhage commencement. The drug was continuously administered for 67.2±4.8 minutes and had no significant effect on glycemic levels, as the increase in glycemia following hemorrhage was 19.9±2.0%. There was no significant difference between the control and post hemorrhage RIST, indicating that cyclosomatostatin administration prevented the occurrence of HDIR following hemorrhage.

Discussion: As previously stated, both acute hemorrhage and exogenous somatostatin (0.16 µg/kg/min) cause insulin resistance that is accountable by HDIR with the direct HISS-independent action being unsuppressed. Cyclosomatostatin (20 µg/kg/min) administered concurrently with somatostatin was able to prevent the occurrence of somatostatin-induced HDIR. Therefore, it was possible to speculate that endogenous somatostatin, which is released in copious amounts in the cat following hemorrhage (Lautt, W. W., Dwan, P. D., Singh, R. R. Control of the hyperglycemic response to hemorrhage to cats. *Can J Physiol Pharmacol.* 60:1618-1623, 1982) was a major mediator of HDIR subsequent to hemorrhage. This postulation proved correct as cyclosomatostatin (20 µg/kg/min) was able to prevent the blockade of HISS following hemorrhage, which was shown by the absence of significant differences between the control and post-hemorrhage RIST indexes (FIG. 12).

What is claimed is:

1. A method of treating HISS-dependent insulin resistance comprising administering a therapeutically effective amount of a somatostatin antagonist to a patient in need thereof.

2. A method of treating hemorrhage induced insulin resistance comprising administering a therapeutically effective amount of a somatostatin antagonist to a patient in need thereof, wherein the hemorrhage induced insulin resistance is HISS-dependent insulin resistance.

3. The method according to claim 1, wherein the somatostatin antagonist is cyclosomatostatin.

4. The method according to claim 3, wherein the therapeutically effective amount of cyclosomatostatin is about 1 to about 1000 µg/kg patient weight.

5. The method according to claim 3, wherein the therapeutically effective amount of cyclosomatostatin is about 1 to about 100 µg/kg patient weight.

6. The method according to claim 3, wherein the therapeutically effective amount of cyclosomatostatin is about 10 to about 50 µg/kg patient weight.

7. The method according to claim 3, wherein the therapeutically effective amount of cyclosomatostatin is about 20 µg/kg patient weight.

8. The method according to claim 1, wherein the somatostatin antagonist is selected from the group consisting of DC-41-33, BIM-23454, SB-710411, cyclo(7-aminoheptanoyl-Phe-D-Trp-Lys-O-benzyl-Thr), AC-178,335 and a combination thereof.

9. The method according to claim 2, wherein the hemorrhage is caused by a surgical intervention.

10. The method according to claim 2, wherein the hemorrhage is caused by an injury.

11. The method according to claim 2, wherein the somatostatin antagonist is cyclosomatostatin.

* * * * *